United States Patent [19]

Breneman et al.

[11] 4,013,905
[45] Mar. 22, 1977

[54] REMOTE ACOUSTIC PROBE

[75] Inventors: Richard Breneman, Benton City; Dwight L. Parry, Richland, both of Wash.

[73] Assignee: Exxon Nuclear Company, Inc., Bellevue, Wash.

[22] Filed: Jan. 9, 1974

[21] Appl. No.: 431,954

[52] U.S. Cl. .............................................. 310/8.3
[51] Int. Cl.² ........................................ H01L 41/08
[58] Field of Search ............ 310/8.3, 8.4, 8.7, 9.1, 310/9.4, 26; 340/8, 10, 17; 73/70

[56] References Cited

UNITED STATES PATENTS

| | | | |
|---|---|---|---|
| 2,799,788 | 7/1957 | Fitzgerald et al. | 310/8.3 |
| 3,137,171 | 6/1964 | Kratz et al. | 310/8.7 |
| 3,374,663 | 3/1968 | Morris | 310/8.4 X |
| 3,638,053 | 1/1972 | Schenk | 310/9.1 X |
| 3,769,532 | 10/1973 | Tocquet | 310/9.1 X |
| 3,806,909 | 4/1974 | Bound | 310/9.1 X |

*Primary Examiner*—Mark O. Budd
*Attorney, Agent, or Firm*—H. N. Wells; F. Donald Paris

[57] ABSTRACT

A self-contained probe for testing of buried pipe by analyzing acoustic emissions produced under increasing stress which comprises an elongated tubular body with a hardened metallic point at one end which is placed against the pipe. The body of the probe also contains an acoustic transducer, a preamplifier, and an integral power supply. The probe receives acoustic emissions from the pipe under test, transforms acoustic signals into electrical voltages, preamplifies those voltages, and transmits them to associated facilities for computer analysis.

10 Claims, 2 Drawing Figures

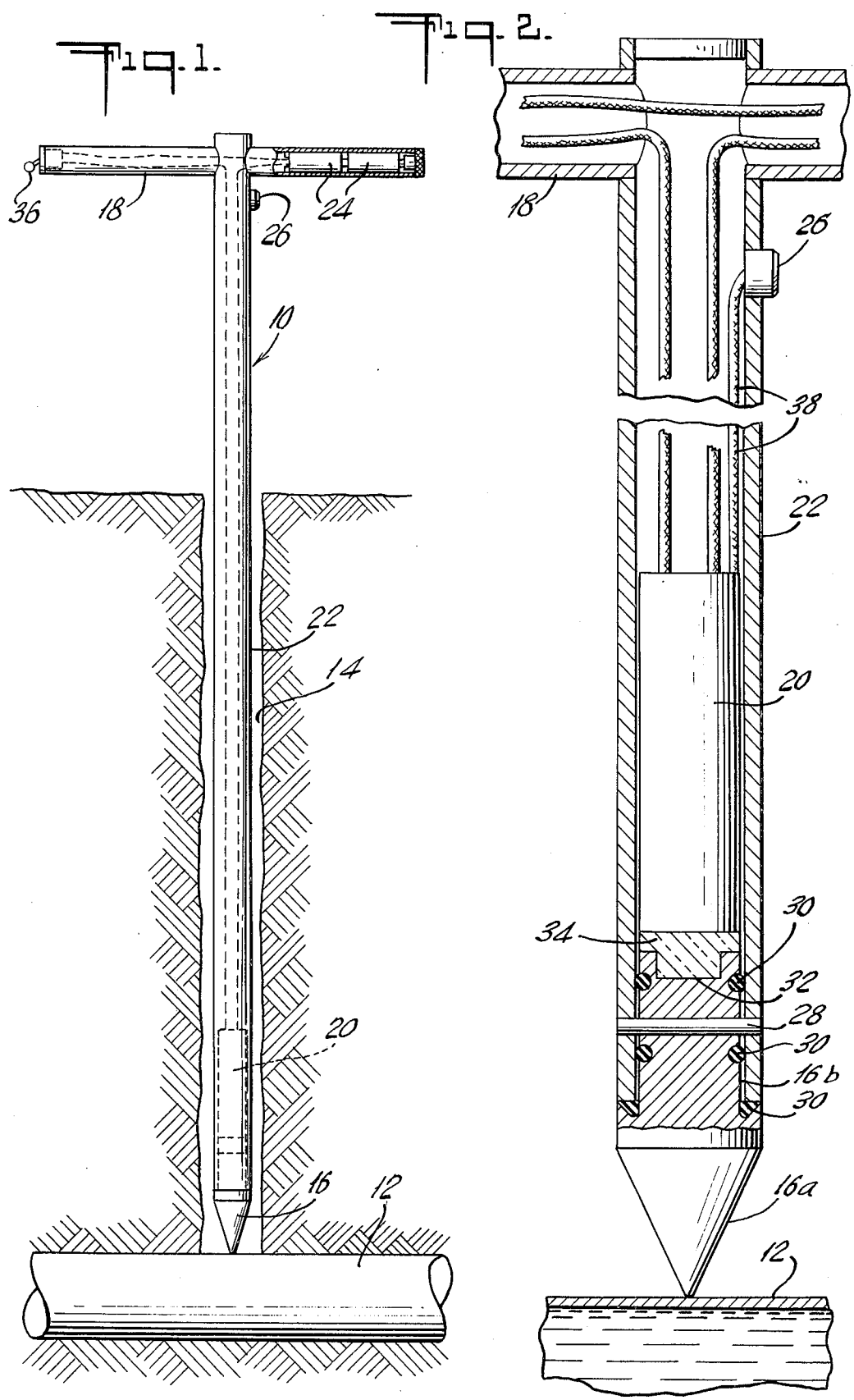

REMOTE ACOUSTIC PROBE

BACKGROUND OF THE INVENTION

The invention relates to acoustic emissions testing of piping, particularly buried piping which is not readily accessible. Specifically, the invention relates to a self-contained probe which permits acoustic emission testing to proceed more rapidly and accurately than has heretofore been possible.

Acoustic emission testing has been developed in recent years, particularly as a means of testing pressure vessels for flaws which could cause mechanical failure. The method as applied to pressure vessels is described in U.S. Pat. No. 3,545,262 and in many articles available in the literature.

Methods of testing buried pipes for leaks have been described in many prior art patents. In particular, the following are noted: U.S. Pat. Nos. 1,881,543; 2,008,934; 3,028,450; 3,055,209; 3,170,152; 3,261,200; 3,289,465; 3,458,656; 3,478,576; 3,508,433; 3,575,040; 3,673,857; 3,691,819. Many of these techniques relied upon the emission of acoustic energy when a fluid contained within the pipe passed through a leak in the wall. These methods differ substantially from that of the present invention in that they generally rely on the measurement of sounds in relatively lower frequency ranges, typically 2HZ to 20 KHZ, created by the passage of fluid through a leak. Acoustic emission testing, as the term is used in the art, is primarily concerned with detecting flaws, not necessarily those which are large enough to represent leaks, but flaws which might cause failure of the pipe when subjected to stress in service or which could lead to leaks. Acoustic emission testing relies, not on the sound produced by fluid passing through a leak, but rather upon sound emitted by the metal itself when subjected to an increasing stress, it being characteristic of such flaws that they cause intermittent bursts of acoustic energy as stress is applied. In contrast to the prior art leak testing, frequencies measured in acoustic emission testing are typically in the range of 25 KHZ to 1 mHZ.

When such a technique is applied to buried piping, considerable difficulties are encountered in the placement of the transducers which are used to receive and properly position, by computer analysis, the location of the flaws contained within the pipe. It will be appreciated that since piping may well be a mile or more in length, it is difficult to properly locate the flaws. Since the acoustic energy is attenuated by passage through the metal, it is necessary to place transducers relatively close together. Generally, a spacing of 200-800 feet is reasonable. With buried piping, positioning of transducers is quite difficult since excavation is required at each point of contact with the pipe, the pipe's surface must be carefully prepared, and transducers must be attached securely in order to accurately receive the acoustic energy transmitted through the pipe. The present invention overcomes the major portion of these difficulties and permits rapid analysis of buried piping for leaks and flaws while eliminating much of the expensive and time-consuming activity heretofore required.

SUMMARY OF THE INVENTION

The invention comprises a self-contained probe for use in acoustic emission testing of buried piping which avoids the need for extensive excavation, surface preparation and attachment of transducers. In its application, small pilot holes are drilled through the surrounding medium, usually earth, over the pipe to be tested at predetermined intervals along the length. The acoustic probes of the invention are installed in the holes, contacting the pipe with a hardened metallic point located at one end of the probe. The hardened metal point facilitates making the secure contact with the metallic pipe which is necessary, penetrating through coatings, rust and other materials which would ordinarily have to be cleared away in order to permit attachment of individual transducers. The hardened metallic point is attached to the body of the probe in such a way as to acoustically isolate the hardened point from the body itself. Acoustic signals received by the hardened point are transferred through the point to an acoustic transducer attached to the point and located within the body member. The acoustic transducer receives acoustic energy from the pipe as it is placed under increasing stress and transforms the acoustic energy into electrical voltages proportional to the amplitude of the acoustic energy received. These electrical voltages are minute, and require preamplification by means of a preamplifier disposed within the body member before being transmitted to associated facilities for analysis of the data received. The preamplifier is disposed within the body member for protection and to minimize the signal losses between the transducer and the preamplifier. The preamplifier is supplied with power from batteries also disposed within the body member, thus producing a completely self-contained acoustic emission probe.

The probe, transducer and amplifier are designed to operate in the frequency range of 25-50 KHZ, which has been found to be an optimum range for buried pipe testing. It is high enough to be above the frequencies of most interfering mechanically created noise, but low enough in frequency to travel a long distance, since the attenuation of an acoustic signal traveling in the metallic pipe is relatively small within this frequency range.

Advantages of the probe in addition to those already described are that there is a minimum of damage to the surrounding area since no significant excavating need be done and thus use of the invention eliminates objections from adjacent property owners relative to the excavations previously required. Since the use of the probe has cut the time required for acoustic emission testing substantially, the cost as been lowered, making the acoustic emission testing procedure more competitive with the techniques of the prior art and permitting the extension of the benefits of this method of testing to additional applications.

BRIEF DESCRIPTION OF THE DRAWINGS

FIG. 1 illustrates the probe of the invention in use.

FIG. 2 is an assembly drawing of the probe of the invention.

DESCRIPTION OF THE PREFERRED EMBODIMENTS

FIG. 1 illustrates the probe of the invention 10 in practical use, measuring the acoustic emission of buried pipe 12. It will be understood that, although the probe is intended primarily for use with buried pipe, other applications for acoustic emission testing could also use the probe of the invention or modifications thereof. It will be appreciated that since a buried pipeline is often 6 feet below the surface, extensive excavation would be required in order to permit access to the pipeline for surface preparation and attachment of acoustic transducers. The probe of the present invention requires little or no removal of earth; typically a narrow core of earth will be drilled out only big enough to accept the probe whose body diameter will be approximately 2 inches. If the probe is to be used more than once in a single spot, it may be convenient to insert a temporary plastic casing inside the holes so that the probe may be withdrawn, used in other locations, and returned for retesting at a particular location. The probe 10 is inserted into the hole 14 in the earth until it contacts the buried pipe 12. Since the hardened metallic point 16 of the probe 10 easily penetrates any coatings, rust, or surface debris which would interfere with the reception of acoustic signals, no special surface preparation or cleaning is required. The point 16 simply needs to contact the pipe firmly. In some instances, it may be sufficient to force the probe through the overlying soil, utilizing the handle portion 18 of the probe which is at the end opposite the hardened point 16 and extends above the surface of the ground when the probe is in use.

The process of acoustic emission testing involves the pressuring of the underground piping 12, generally at a constant rate, so that any flaws or leaks present in the pipe will generate noise in a characteristic fashion as the stress on the pipe increases. Cyclic pressurization of the pipe and over-head loading with a heavy vehicle have also been successfully applied as means of stressing the pipe. It is known in the prior art that the emission of sound induced by the presence of flaws in metal releases an intermittent burst of acoustic energy which can be detected, in contrast to a continual background noise which is otherwise received. These intermittent bursts of acoustic energy increase in frequency of occurrence and intensity as the pipe approaches its point of failure. Thus, the method permits the location and detection of flaws and also the determination of the severity of the flaws; that is, certain minor flaws may be detected which are not serious and create no danger of rupture of the pipe.

Once the probe 10 is in position against the pipe 12 and the pipe is under increasing stress, signals received by the hardened point are translated into electrical voltages by an acoustic transducer within the vertical body of the pipe (not shown) and attached to the hardened point. The point itself is acoustically isolated from the remainder of the probe in order to avoid the introduction of extraneous mechanical noises. The signals produced by the acoustic transducer are on a very low level, on the order of 10 to 100 micro volts. Accordingly it is necessary to amplify them for transmission to external facilities for analysis. In the invention, a preamplifier 20 is located within the vertical body 22 of the probe and immediately above the acoustic transducer, not shown, in order to avoid any signal losses or introduction of extraneous noise. The preamplifier 20 is operated by a battery pack 24 contained within the probe, although it could be powered from an external source if desired. The signal produced by the preamplifier 20 leaves the probe via the connector 26 and is transmitted to nearby equipment for analysis.

It will be appreciated that the probe has substantial advantage over the prior art technique of excavating, cleaning of the pipe and attaching of acoustic transducers. The probe is simpler to use and it provides much more rapid and certain results when compared to the prior art method.

Acoustic energy produced by the pressuring of pipe is typically broad band in frequency content. However, the probe, transducer and amplifier are designed to operate within the frequency range of 25–50 KHZ. It has been found that this frequency range is particularly suited to testing of buried pipe. The frequency range is high enough to avoid most interfering mechanically created noise, but low enough in frequency to allow a long distance in the spacing between the probes since the attenuation of acoustic energy traveling in metal pipe is relatively small in the 25–50 KHZ region.

FIG. 2 shows an assembled view of the probe of the invention. Its principal portions are the tubular body member 22, which is long enough to reach the buried pipe to be tested, a tubular handle member 18 mounted normal to the body member 22 at one end, the end extending above ground when the probe is in use. The signal receiving portion of the probe consists of the hardened point 16 which is in itself comprised of two portions, a conical shaped hardened point 16a for contacting the buried piping and an essentially cylindrical shank portion 16b which extends within the body member 22 and is secured thereto by means of a resilient pin 28 which passes through the body member 22 and the shank portion 16b of the hardened point 16. The resilient pin 28 not only secures the point to the body, but at the same time provides acoustic isolation of the point 16 from the body 22 in order to minimize the introduction of mechanical noise. Other acoustic isolation is provided by O rings 30 spaced along the shank portion and the shoulder between the conical point 16a and the end of the body member 22. A recess 32 is provided at the end of the shank member opposite the hardened point for firmly securing an acoustic transducer 34. It has been found that piezoelectric transducers having a resonant frequency of 25–50 KHZ are particularly useful for this service. However, it is also within the scope of the invention to use transducers in the range of 100 KHZ to 1 mHZ resonant frequency. It is also within the scope of the invention to use other transducers, including the magnetostrictive and capacitive types, as well as the piezoelectric type. The signals received through the hardened point 16a from the pipe 12 as it is subjected to increasing stress are of a very low level. The transducer 34 produces a very low level of electrical voltage corresponding to the signals received. The preamplifier 20 which is used to convert and amplify the electrical voltages for transmission to analysis facilities located nearby is positioned directly above the acoustic transducer 34 within the body member 22. It is a special transistorized amplifier unit which accepts an input at the level of 10–100 microvolts and produces as an output voltages in the range of 0.01 to 0.1 volts. The preamplifier is powered by a battery pack 24 conveniently located in the handle portion of the probe for easy access. A switch 36 to turn on or off the preamplifier is also conveniently located on the probe handle (see FIG. 1). Output of the preamplifier 20 passes through leads 38 and out of the probe 10 through connector 26 to nearby equipment for analysis.

The assembled probe is simple in construction yet provides an exceedingly convenient tool for contacting buried piping and measuring the acoustic emissions produced by increasing stress on the pipe, and thereby detecting the presence of flaws or leaks.

The foregoing description of the preferred embodiment is for illustration of the invention and is not intended to limit the scope of the invention as defined by the claims which follow.

What is claimed is:

1. An apparatus for sensing acoustic emissions from a member under stress comprising:
   a. an elongated tubular body;
   b. a hard metallic pointed member disposed at one end of said body for receiving and transmitting said acoustic emissions from said member when in firm and direct contact therewith;
   c. acoustic transducer means in said body acoustically coupled to said pointed member for receiving said acoustic emissions through said pointed member from said member under stress when said pointed member is in direct contact therewith and converting said emissions into electrical voltages proportional to the amplitude of the emissions received; and
   d. means for acoustically isolating said pointed member and said acoustic transducer means from said tubular body.

2. The apparatus of claim 1, further comprising:
   e. a preamplifier means disposed within said body and electrically directly connected to said acoustic transducer means for increasing the voltages produed by said transducer means to a level suitable for transmission; and
   f. a power supply for said preamplifier means.

3. The apparatus of claim 1 wherein said hard metallic pointed member is conical at its extremity for facilitating easy egress of said point through any medium on said member.

4. The apparatus of claim 1 wherein said acoustic transducer means are selected from the group consisting of piezoelectric, magnetostrictive and capacitive transducers.

5. The apparatus of claim 2 wherein said power supply for said preamplifier means is a battery means disposed within said apparatus thereby providing a self-contained probe for sensing and transmitting acoustic emissions from pipe.

6. The apparatus of claim 1 wherein said member comprises a pipe.

7. The apparatus of claim 1 wherein said acoustic transducer means is located directly adjacent said pointed member.

8. The apparatus of claim 1 wherein the acoustic isolating means comprises resilient means which also secures said pointed member to said tubular body.

9. An apparatus for sensing acoustic emissions from a member under stress comprising:
   a. an elongated tubular body;
   b. a hard metallic pointed member disposed at one end of said body for receiving said acoustic emissions from said member when in direct contact therewith, said pointed member comprising a cylindrical shank portion longitudinally disposed in said tubular body and having a passageway laterally extending through said shank portion;
   c. acoustic transducer means in said body acoustically coupled to said pointed member for receiving said acoustic emissions through said pointed member from said member under stress when said pointed member is in direct contact therewith and converting said emissions into electrical voltages proportional to the amplitude of the emissions received; and
   d. means for acoustically isolating said pointed member and said acoustic transducer means from said tubular body, comprising a resilient pin extending through said passageway for securing said pointed member to said tubular body and acoustically isolating it therefrom.

10. The apparatus of claim 9 wherein the acoustic isolation means comprises gasket means disposed between said shank portion and said tubular body.

* * * * *